(12) United States Patent
Tian et al.

(10) Patent No.: US 8,974,734 B2
(45) Date of Patent: Mar. 10, 2015

(54) ELECTRONIC NOSE DEVICE

(71) Applicant: EPS Bio Technology Corp., Hsinchu Science Park (TW)

(72) Inventors: Jun-Hao Tian, Hsinchu Science Park (TW); Jian-Hua Chen, Hsinchu Science Park (TW); Chi-Zuo Chu, Chung Ho (TW); Wei-Jen Ho, Chu Pei (TW); Li-Jin Kang, Tao Yuan (TW); Yu-Lun Wang, Hsinchu Science Park (TW); Meng-Erh Li, Hsinchu Science Park (TW)

(73) Assignee: EPS Bio Technology Corp., Hsinchu (TW)

( * ) Notice: Subject to any disclaimer, the term of this patent is extended or adjusted under 35 U.S.C. 154(b) by 0 days.

(21) Appl. No.: 13/946,629

(22) Filed: Jul. 19, 2013

(65) Prior Publication Data
US 2014/0023557 A1    Jan. 23, 2014

(30) Foreign Application Priority Data

Jul. 20, 2012  (TW) .............................. 101126266 A

(51) Int. Cl.
*G01N 15/06*     (2006.01)
*G01N 33/00*     (2006.01)
*G01N 33/48*     (2006.01)

(52) U.S. Cl.
CPC .................................. *G01N 33/0027* (2013.01)
USPC ................... 422/83; 422/98; 422/50; 422/62; 436/43; 436/178

(58) Field of Classification Search
USPC ....................................................... 422/83, 98
See application file for complete search history.

(56) References Cited

U.S. PATENT DOCUMENTS 6,085,576 A * 7/2000 Sunshine et al. ............. 73/29.01
7,089,780 B2   8/2006 Sunshine et al.

FOREIGN PATENT DOCUMENTS

| CN | 102300502 A | 12/2011 |
|----|-------------|---------|
| JP | 2000-333487 | 11/2000 |
| JP | 2002-538457 | 11/2002 |
| JP | 2012-510319 | 5/2012 |
| TW | 537879 B | 6/2003 |
| TW | M305663 U | 2/2007 |
| TW | 201219009 | 5/2012 |

* cited by examiner

*Primary Examiner* — Brian J Sines
(74) *Attorney, Agent, or Firm* — Muncy, Geissler, Olds & Lowe, P.C.

(57) ABSTRACT

An electronic nose device is disclosed in an embodiment of the invention. The electronic nose device includes a fan module, a gas molecule sensor module, a control unit and an output unit. The fan module is used to pump air actively to the gas molecule sensor module. The gas molecule sensor module detects the air pumped into by the fan module. The gas molecule sensor module at least includes a gas molecule sensor which is covered with a compound. The compound is used to combine preset gas molecules. The control unit controls the fan module to suck air into the electronic nose device. Then the fan module transmits an air current to the gas molecule sensor module to generate a detected data. The output unit calculates the detected data to generate a calculation result and outputs an indicating signal to an operator or compatible host computer according to the calculation result.

16 Claims, 3 Drawing Sheets

ELECTRONIC NOSE DEVICE

This application claims the benefit of the filing date of Taiwan Application Ser. No. 101126266, filed on Jul. 20, 2012, the content of which is incorporated herein by reference.

BACKGROUND OF THE INVENTION

1. Field of the Invention

The invention relates to an electronic device, and more particularly, to an electronic nose device.

2. Description of the Related Art

Prior electronic noses have been generally applied to many testing and industrial fields so that they have large size and are not suitable for home and business applications.

Some small electronic noses are separated into a gas storage type (TW patent No. 537879), a passive type (TW patent No. M305669) and a series flow meter type (TW publication No. 201219009).

A gas storage type electronic nose needs to set up a storage space and a complicated air pipe system to reach a purpose of generating a stable air current for detection.

A passive type electronic nose cannot detect air, such as spontaneous stink from a toilet, since it is not equipped with a pump to pump air in from the outside.

A series flow meter type electronic nose needs to add a flow detector to compensate an unstable air current.

SUMMARY OF THE INVENTION

An object of the invention is to provide an electronic nose device that can detect air without using a flow meter.

An object of the invention is to provide an electronic nose device that can suck air with a stable air current to improve the detection precision.

An electronic nose device of an embodiment of the invention is to improve a fan control circuit of a prior electronic nose using a flow meter. The embodiment of the electronic nose device calculates an air flow rate according to a relation between excitation and back-EMF (back electromotive force) from an operation of a fan module (such as a brushless motor). Therefore the structure of an active-extraction-type electronic nose can be simplified. Thus the size of the active-extraction type electronic nose can be reduced and the application of the electronic nose device can become popular.

An electronic nose device of another embodiment of the invention includes a fan module, a gas molecule sensor module, a control unit and an output unit.

The fan module includes an actuator and an air current pushing mechanism. The fan module is used to actively pump air into the gas molecule sensor module.

The gas molecule sensor module detects the air pumped into by the fan module. The gas molecule sensor module at least includes a gas molecule sensor covered with a compound. The compound is used to combine at least a preset gas molecule.

The control unit includes a motor control unit and a gas sensor controller. The motor control unit includes a motor excitation circuit and a back-EMF (back electromotive force) detection circuit. The gas sensor controller includes a sensor excitation circuit and a reaction detector. The control unit controls the fan module to suck air into the electronic nose device. Then the fan module transmits an air current to the gas molecule sensor module to generate a detected data.

The output unit is used to calculate the detected data to generate a calculation result and output an indicating signal to an operator or a compatible host computer according to the calculation result. Further the output unit includes a calculator for calculating the detected data to generate the calculation result.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

In this specification and the appended claims, some specific words are used to describe specific elements. It should be understood by those who are skilled in the art that some hardware manufacturer may use different names to indicate the same element. In this specification and the appended claims, elements are not differentiated by their names but their functions. As used herein and in the claims, the term "comprising" is inclusive or open-ended and does not exclude additional unrecited elements, compositional components, or method steps. Besides, the term "coupling", when used herein and in the claims, refers to any direct or indirect connection means. Thus, if the specification describes a first device is coupled to a second device, it indicates that the first device can be directly connected (via signal connection, including electrical connection, wireless transmission, optical transmission, etc.) to the second device, or be indirectly connected to the second device via another device or connection means.

As used herein and in the claims, the term "and/or" includes any and all combinations of one or more of the associated listed items. The use of the terms "a" and "an" and "the" and similar referents in the context of describing the invention are to be construed to cover both the singular and the plural, unless otherwise indicated herein or clearly contradicted by context.

Figure 1A:
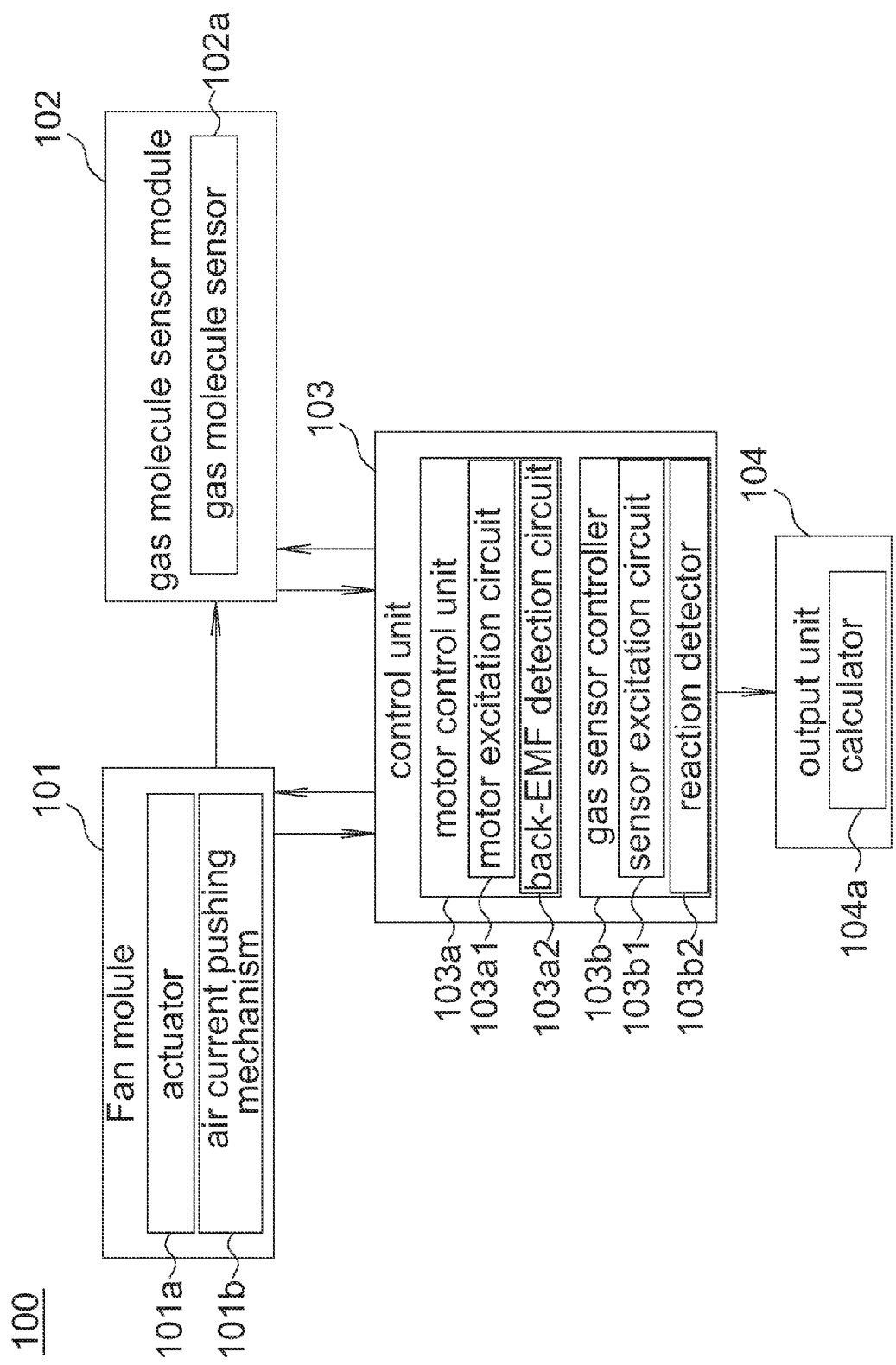
FIG. 1A shows a block diagram of an electronic nose device of an embodiment according to the invention.

FIG. 1A shows an electronic nose device of an embodiment of the invention. As shown in FIG. 1A, the electronic nose device 100 includes a fan module 101, a gas molecule sensor module 102, a control unit 103 and an output unit 104.

The fan module 101 at least includes an actuator 101a and an air current pushing mechanism 101b. The fan module 101 actively pumps air into the gas molecule sensor module 102 for detection. Further the actuator 101a is used to actuate the fan module 101 while the air current pushing mechanism 101b pushes air to generate the air current.

The gas molecule sensor module 102 detects the incoming air pumped by the fan module 101. The gas molecule sensor module 102 at least includes a gas molecule sensor 102a. The gas molecule sensor 102a is covered with a compound for combining preset gas molecules and detects air to generate an electrical signal (such as voltage, current, frequency or phase).

The control unit 103 includes a motor control unit 103a and a gas sensor controller 103b. The motor control unit 103a is used to control the fan module 101. The motor control unit 103a includes a motor excitation circuit 103a1 and a back-EMF (back electromotive force) detection circuit 103a2. The motor excitation circuit 103a1 drives a motor of the fan module 101. The back-EMF (back electromotive force) detection circuit 103a2 detects a back-EMF generated by the motor of the fan module 101. The gas sensor controller 103b is used to control the gas molecule sensor module 102. The gas sensor controller 103b includes a sensor excitation circuit 103b1 and a reaction detector 103b2. The sensor excitation circuit 103b1 drives the gas molecule sensor module 102 while the reaction detector 103b2 detects a sensing result of the gas molecule sensor module 102. The control unit 103 controls the fan module 101 to suck air into the electronic nose device 100. Then the fan module 101 transmits an air current to the gas molecule sensor module 102 to generate a detected data.

The output unit 104 includes a calculator 104a. The calculator 104a calculates the detected data to generate a calculation result. The output unit 104 outputs an indicating signal to an operator or a compatible host computer.

In an embodiment, examples of the gas molecule sensor include, without limitation, a piezoelectric quartz crystal, surface acoustic wave material, electrochemistry material, optical fiber, surface plasma resonance and metal oxide semiconductor.

In an embodiment, the above mentioned compound for combining at least a preset gas molecule may be ZnO, NiO, Fe2O3, TiO2, CdSnO3, SnO2, WO3 and Au nanoparticle; WO3+SnO2, WO3+ZnO, TiO2+ZnO and WO3+Fe2O3 hybrid nanoparticle; CYS-LYS-ARG-GLN-HIS-PRO-GLY-LYS-ARG-CYS; LYS-ARG-GLN-HIS-PRO-GLY-LYS-ARG(KRQHPGKR); LYS-ARG-GLN-HiS-PRO-GLY (KRQHPG); HAC01-Acid; TN-Ammonia; DH31-Amine-acid; P1-Aromatic; A1N-Amine-Mercaptans; A5N-Mercaptans; other compounds, anion or cation substrates (receptors), peptides; or its corresponding antibodies which can be combined with Indole or Ammonia.

In an embodiment, a kind of peptide which can be combined with Indole or Ammonia may be a predetermined protein domain (including peptide). The predetermined protein domain may use any kinds of combination methods to catch material in the air which can be identified to reach a function of air identification. In another embodiment, the predetermined protein area may be from a protein substrate wherein the protein substrate may include a hydrophobic interaction protein, a hydrogen bonding protein, or a plant hormone binding protein and the protein substrate may further include a recombinant functional homologous of the protein substrate.

In another embodiment, the protein substrate may be a transport inhibitor response 1-like protein (TIR1-like protein).

In an embodiment, examples of the actuator include, without limitation, a direct-current brushless motor, an alternating current induction motor and a triple-phase alternating current synchronous motor.

In an embodiment, examples of the air current pushing mechanism include, without limitation, a fan blade, a propeller and a turbine.

In an embodiment, the output unit may be a light signal indicator, such as a light emitting diode, a lamp, an incandescent lamp or a laser.

In an embodiment, the output unit may be an image display device, such as a liquid crystal display or an organic light emitting diode display.

In an embodiment, the output unit may be an audio signal indicator, such as a buzzer or a speaker.

In an embodiment, the output unit may be a wireless transmission interface, such as blue tooth or Wifi.

In an embodiment, the output unit may be a wired transmission interface, such as Universal Serial Bus (USB), Universal Asynchronous Receiver/Transmitter (UART) or Serial Peripheral Interface (SPI).

Figure 1B:
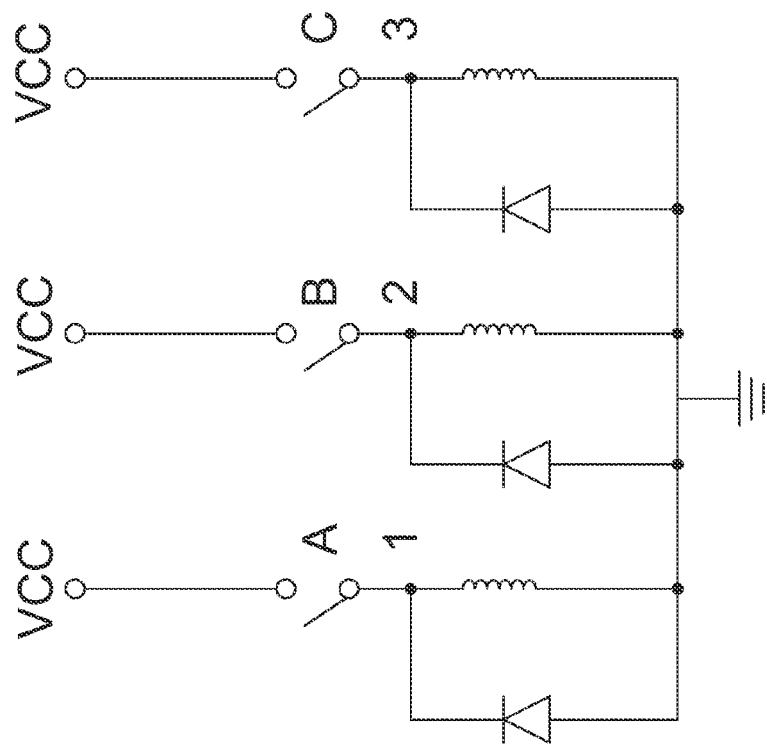
FIG. 1B shows a schematic diagram of a back-EMF circuit of an embodiment according to the invention.

In an embodiment, the fan module 101 drives the air to generate an air current. During operation, the back-EMF on a magnetic coil is related to an acting force between the air current pushing mechanism 101b (such as a propeller) and air so that an air flow rate can be calculated according to an exciting current, a rotation speed and a back-EMF. An embodiment of the back-EMP (back electromotive force) detection circuit 103a2 is as shown in FIG. 1B. As shown in FIG. 1B, the back-EMF detection circuit 103a2 includes three switches A, B, C, three coils and three diodes. Assuming a motor rotor of the fan module 101 is a permanent magnet and a motor stator of the fan module 101 includes three coils. The control unit 103 turns on the three switches A, B, C sequentially so as to generate a rotated magnetic field to rotate the rotor.

When the control unit 103 turns off the switches A, B, C and the motor rotor continues rotating, according to the Lenz's law, the magnetic flux of the coils generates an induced current due to the rotation of the motor rotor and generates an induced electromotive force between two ends of the coil (such as the node 1 to the ground). Here, the induced electromotive force is a back-EMF.

According to the Faraday's law of electromagnetic induction, the amount of the induced electromotive force is in direct proportion to the variation of the magnetic flux so that the rotation speed can be calculated according to the back-EMF. Therefore, before a motor leaves a factory, relations of several back-EMF values and several rotation speeds can be recorded as recording values. Therefore the electronic nose device 101 can use a back-EMF to calculate a corresponding rotation speed according to the recording values. In this way, an air flow rate in a preset unit can be calculated based on an exciting current, a rotation speed, a back-EMF, etc and other related information.

The detected data generated by the gas molecule sensor module 102 may further be calibrated according to the air flow rate. In an embodiment, an equation for calculating a mass change mcal of a calibrated detected data is listed below:

$$m\text{cal} = \Delta m / VK, \quad (1)$$

wherein $\Delta m$ denotes a mass change after the predetermined protein domain adsorbs an air molecule, V denotes a back-EMF and K denotes a constant of an air flow rate which is determined by the mechanism design of the electronic nose device 100.

Then, $m_{cal}$ is divided by M ($m_{cal}/M$) to generate an adsorbed air molecule amount of the gas molecule sensor module 102 that is a real air molecule content of a detected target. Here, M denotes an air molecule amount of the detected target.

Therefore, the electronic nose device of embodiments of the invention can achieve the effect of accurately detecting an air molecule and simplify the structure of an active-extraction-type electronic nose device. Thus the electronic nose device 100 of the invention can be in widespread use.

In an example, the electronic nose device 100 is installed in a toilet and used to detect ammonium and mercaptan. In this regard, the electronic nose device 100 can monitor an odor of the toilet and therefore a central monitoring host can automatically inform a cleaner to clean the toilet or automatically spray fragrance for the toilet to keep the toilet clean.

In another example, the electronic nose device 100 is fixed on a diaper for a pet or a child and used to detect ammonium and mercaptan. In this regard, the electronic nose device 100 can monitor whether a pet or a child excretes and indicate if the diaper needs to be replaced.

In another example, in a sanatorium, the electronic nose device 100 is fixed on an adult diaper for a person in care and used to detect ammonium and mercaptan. In this regard, the electronic nose device 100 can automatically monitor whether an adult diaper needs to be replaced and generate the indicating signal or informs a central monitor host to replace the adult diaper. In this way, the electronic nose device 100 can save time for a routine check (if an adult diaper needs to be replaced) and also improves dignity for the people in care.

Figure 2:
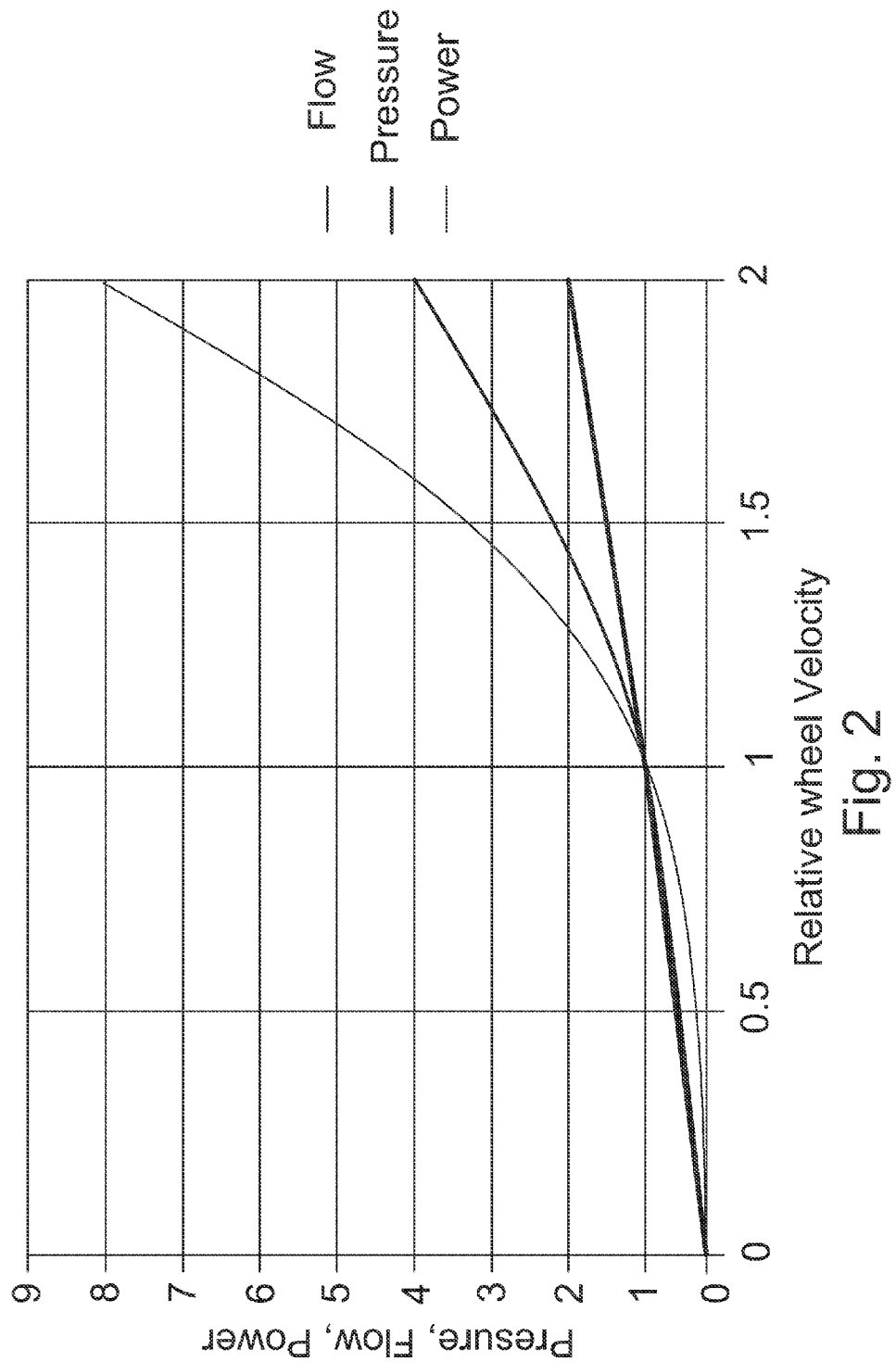
FIG. 2 shows a waveform diagram indicating a relation between a fan rotation speed and an air flow rate.

FIG. 2 shows a waveform diagram indicating a relation between a fan rotation speed and an air flow rate. As shown in FIG. 2, a relation of the excitation magnetic, back-EMF and the air flow rate of the electronic nose device 100 is listed below:
The air flow rate is in direct proportion to the amount of the fan rotation speed with a fixed fan diameter of the fan module 101.

In an embodiment, a direct-current brushless motor of the fan module 101 may detect a back-EMF of a preset coil to obtain a rotation speed. The motor control unit 103a may perform a fixed speed and current control or directly feedback a rotation speed data to subsequent calculation.

While certain exemplary embodiments have been described and shown in the accompanying drawings, it is to be understood that such embodiments are merely illustrative of and not restrictive on the broad invention, and that this invention should not be limited to the specific construction and arrangement shown and described, since various other modifications may occur to those ordinarily skilled in the art.

What is claimed is:

1. An electronic nose device, comprising:
a fan module for actively pumping air;
a gas molecule sensor module, coupled to the fan module, wherein the gas molecule sensor module comprises a gas molecule sensor which is covered with a compound for combining a preset gas molecule;
a control unit, coupled to the fan module and the gas molecule sensor module, wherein the control unit controls the fan module to suck air and transmits an air current to the gas molecule sensor module to generate a detected data; and
an output unit for calculating the detected data to generate a calculation result and outputting an indicating signal to an operator or a compatible host computer according to the calculation result,
wherein the compound for combining a preset gas molecule is a predetermined protein domain for using at least a combination method to catch material in the air which can be identified to reach air identification function.

2. The electronic nose device according to claim 1, wherein the fan module drives the air to generate the air current, the output unit calculates an air flow rate of the air current according to an exciting current, a rotation speed and a back-EMF, and calibrates the detected data according to the flow rate of the air current.

3. The electronic nose device according to claim 1, wherein the compound for combining a preset gas molecule is anion or cation substrates (receptors), or peptides or its corresponding antibodies.

4. The electronic nose device according to claim 1, wherein the fan module comprises:
an actuator for actuating the fan module; and
an air current pushing mechanism for pushing air to generate the air current.

5. The electronic nose device according to claim 1, wherein the control unit comprises:
a motor control unit for controlling the fan module; and
a gas sensor controller for controlling the gas molecule sensor module.

6. The electronic nose device according to claim 5, wherein the motor control unit comprises:
a motor excitation circuit for driving a motor of the fan module; and
a back-EMF detection circuit for detecting a back-EMF generated by the motor of the fan module.

7. The electronic nose device according to claim 5, wherein the gas sensor controller comprises:
a sensor excitation circuit for driving the gas molecule sensor module; and
a reaction detector for detecting a sensing result of the gas molecule sensor module.

8. The electronic nose device according to claim 1, wherein the output unit comprises a calculator for calculating the detected data to generate the calculation result.

9. The electronic nose device according to claim 1, wherein the gas molecule sensor is one of piezoelectric quartz crystal, surface acoustic wave material, electrochemistry material, optical fiber, surface plasma resonance and metal oxide semiconductor; wherein the actuator is one of a direct-current brushless motor, an alternating current induction motor and a triple-phase alternating current synchronous motor; wherein the air current pushing mechanism is one of a fan blade, a propeller and a turbine; wherein the output unit is one of a light signal indicator, a light emitting diode, a lamp, an incandescent lamp and a laser; wherein the output unit is one of an image display device, a liquid crystal display and an organic light emitting diode display; wherein the output unit is one of an audio signal indicator, a buzzer and a speaker; wherein the output unit is one of a wireless transmission interface, blue tooth and Wifi; and wherein the output unit is one of a wired transmission interface, USB, UART and SPI.

10. The electronic nose device according to claim 1, which is used for detecting air from a diaper.

11. The electronic nose device according to claim 1, wherein the fan module drives the air to generate the air current and the output unit calculates an air flow rate of the air current according to an exciting current, a rotation speed and a back-EMF.

12. The electronic nose device according to claim 6, wherein the back-EMF detection circuit includes a plurality of switches and a plurality of coils corresponding to the switches separately, and wherein when the control unit turns off the switches and the rotor continues rotating, magnetic flux of the coils generates an induced current due to a rotation of a rotor to generate the back-EMF between two ends of each of the coils.

13. The electronic nose device according to claim 12, wherein an amount of the back-EMF is in direct proportion to a variation of the magnetic flux so that a rotation speed can be calculated by the back-EMF.

14. An electronic nose device, comprising:
a fan module for pumping air;
a gas molecule sensor module, coupled to the fan module, wherein the gas molecule sensor module comprises a gas molecule sensor which is covered with a predetermined protein domain for combining a preset gas molecule;

a control unit, coupled to the fan module and the gas molecule sensor module, wherein the control unit controls the fan module to suck air and transmits an air current to the gas molecule sensor module to generate a detected data; and an output unit for calculating the detected data to generate a calculation result and outputting an indicating signal to an operator or a compatible host computer according to the calculation result, wherein the control unit includes a back-EMF detection circuit and the back-EMF detection circuit includes a plurality of switches and a plurality of coils corresponding to the switches separately, and wherein when the control unit turns off the switches and the rotor continues rotating, magnetic flux of the coils generates an induced current due to a rotation of a rotor to generate a back-EMF between two ends of each of the coil.

15. The electronic nose device according to claim 14, wherein the fan module drives the air to generate the air current, the output unit calculates an air flow rate of the air current according to an exciting current, a rotation speed and a back-EMF, and calibrates the detected data according to the air flow rate of the air current.

16. The electronic nose device according to claim 15, wherein an amount of the back-EMF is in direct proportion to a variation of the magnetic flux so that a rotation speed can be calculated by the back-EMF.

\* \* \* \* \*